United States Patent [19]
Craig

[11] Patent Number: 5,730,147
[45] Date of Patent: Mar. 24, 1998

[54] COMBINED THERMOMETER AND FECAL SAMPLING APPARATUS

[76] Inventor: Robert J. Craig, 711 Williams Lake Rd., Pineville, La. 71360

[21] Appl. No.: 584,086

[22] Filed: Jan. 11, 1996

[51] Int. Cl.$^6$ .................................................. A61B 5/00
[52] U.S. Cl. ................................. 128/736; 128/757
[58] Field of Search ........................ 128/736, 757–759

[56] References Cited

U.S. PATENT DOCUMENTS

| | | | |
|---|---|---|---|
| D. 315,520 | 3/1991 | Murray | D10/57 |
| 4,344,419 | 8/1982 | Burgin | 128/18 |
| 4,813,790 | 3/1989 | Frankel et al. | 128/736 |
| 5,013,161 | 5/1991 | Zaragoza | 374/208 |
| 5,017,019 | 5/1991 | Pompei | 128/736 |
| 5,222,809 | 6/1993 | Ehrenkranz | 374/141 |
| 5,265,620 | 11/1993 | Fisher | 128/736 |
| 5,335,669 | 8/1994 | Tihon | 128/736 |

*Primary Examiner*—Max Hindenburg
*Attorney, Agent, or Firm*—John M. Harrison

[57] ABSTRACT

A combined thermometer and fecal sampling apparatus which allows concurrent sampling of a fecal specimen and measuring of body temperature from a single penetration of the rectum. In a preferred embodiment the apparatus includes a proximal end, or handle which is enlarged to facilitate handling and encloses a digital thermometer with a switch cover on one end of the handle covering a switch that activates the thermometer. A temperature display window is provided in the handle of the device for displaying temperature and in a most preferred embodiment, grip splines or knurls are provided on the handle to facilitate gripping and rotating the apparatus to collect the fecal sample. An elongated, hollow probe extends from the handle to a proximal end that terminates in a fecal sampler which is characterized by an ovoid loop having concave collection surfaces defining an ovoidal cavity. Wiring extends from the thermometer through the hollow interior of the probe and terminates in a thermistor positioned above the fecal sampler in a probe window for sensing the temperature of the rectum. This temperature is displayed in the temperature display window in the handle of the apparatus.

12 Claims, 1 Drawing Sheet

COMBINED THERMOMETER AND FECAL SAMPLING APPARATUS

FIELD OF THE INVENTION

This invention relates to fecal sampling devices and thermometers and more particularly, to a combined thermometer and fecal sampling apparatus which facilitates concurrent sampling of a fecal specimen and measuring of body temperature from a single penetration of the rectum. In a preferred embodiment of the invention the apparatus includes an enlarged proximal handle end suitable for handling and provided with a temperature window and a thermometer for displaying the temperature of a patient. In a most preferred embodiment the handle of the apparatus includes a flexible rubber or plastic cover placed over a thermometer switch mounted on the thermometer and extending through a cover or cap threaded in the handle. Multiple longitudinal grip splines or knurls facilitate a sure grip on the handle and rotating the apparatus to collect the fecal sample. An elongated, hollow probe extends from the handle of the apparatus and terminates in a fecal sampler which is characterized by an ovoid loop having concave collection surfaces to facilitate collection of a fecal sample in the ovoidal cavity defined by the concave collection surfaces in the ovoidal loop. The hollow interior of the probe receives wiring from the thermometer, which wiring terminates in a thermistor positioned in a probe window above the fecal sampler for sensing the temperature of the rectum at a desired depth of penetration. This temperature is determined by the thermometer located inside the handle of the apparatus and is displayed in the temperature display window upon pressing of the thermometer activation button covered by the flexible switch cover located in the extreme end of the handle.

One of the problems which exists in obtaining fecal samples and measuring the temperature of animals such as dogs and cats, is the emotional and physical trauma involving penetration of the rectum with the measuring or sampling device. These procedures typically include fecal ovoid collection by means of an elongated plastic member having ovoid loops of varying size on each end and separate physiologic temperature measurement, which dual probing is highly stressful to pets. It is believed that the combined thermometer and fecal sampling apparatus of this invention will greatly minimize stress levels in these animals because of the reduced time involved for combining the fecal ovoid sample collection and temperature measuring operations in a single procedure. Another problem realized during dual rectal probing for temperature measurement and fecal ovoid collection in animals is that of the requirement of cleaning two instruments, thereby increasing time and labor costs involved. Still another problem is that of using fecal collection ovoid loops and similar devices which are not uniform and smooth, therefore causing additional discomfort to the animal and adding to the stress involved.

DESCRIPTION OF THE PRIOR ART

Various devices are known in the art for determining the temperature of animals. An "Electronic Clinical Thermometer" is detailed in U.S. Pat. No. 5,013,161, dated May 7, 1991, to Zaragoza et al. The thermometer includes a hollow probe extending outwardly in a distal direction and a temperature-sensing element located at the distal end of the probe. The housing holds a digital display and electrical apparatus in electrical communication with the temperature sensing element for converting the temperature measured by the temperature sensing element into a read-out on the display element. A resilient, soft cover covers the probe in a portion of the housing to form a gripping surface for the user while allowing visualization of the display element. U.S. Pat. No. 5,222,809, dated Jun. 29, 1993, to Ehrenkranz details a "Method and Apparatus For Obtaining the Core Body Temperature of An Infant". The device employs a readily deployed collection surface contiguous with a sump or reservoir, into which collected urine contacts a superabsorbent powder. Affixed to the reservoir is a temperature sensor for indicating the maximum temperature of the urine and thus, the core body temperature of the donor. A "Fecal Specimen Sampling and Temperature Measuring Device" is detailed in U.S. Pat. No. 5,265,620, dated Nov. 30, 1993, to David W. Fisher. The sampling device of this invention includes a body portion or sheath fitted with a partially cut-away distal end to form a scoop. The thermometer is inserted in an annual bore in the sheath. U.S. Pat. No. 5,335,669 to Tihon, et al and dated Aug. 9, 1994, details a "Rectal Probe With Temperature Sensor". The device includes a longitudinal axis, around which is mounted an inflatable, low pressure compliant balloon having a temperature element associated with a wall thereof, a device for holding the probe at a proper position within a patient's rectum and apparatus for inflating the balloon when it is properly positioned, to put the temperature element in intimate contact with the anterior side of the rectum. Design Pat. No. 315,520 to Murray, et al, details a "Veterinary Digital Thermometer" which has a shaped handle and an elongated probe for insertion in the rectum of the animal.

Accordingly, it is an object of this invention to provide a new and improved combined thermometer and fecal sampling apparatus which is characterized by a proximal or handle portion that encloses a thermometer and incorporates a display window for viewing the temperature and a probe extending from the handle, which probe terminates in an ovoid loop having concave collection surfaces for collecting fecal material.

Another object of this invention is to provide a temperature sensing and fecal collection device combined in a single instrument which includes an enlarged handle and threaded handle cover or cap for enclosing a digital thermometer and an elongated probe extending from the handle and terminating in a fecal collection ovoid loop having opposed concave collection surfaces, with a thermistor located in a window of the probe and wired to the digital thermometer, for both sensing the temperature of, and collecting a fecal sample from, the animal.

Still another object of this invention is to provide a combined temperature sensing and fecal collection device having an enlarged cylindrical handle for receiving a digital thermometer, a flexible rubber or plastic sheath positioned on a cap threaded in the end of the handle over the thermometer activation button and an elongated, hollow probe extending from the handle and containing a thermistor connected to the thermometer, with an ovoid loop having opposed, concave, surface tension-inducing collection surfaces provided at the extending end of the probe. Accordingly, the temperature of the rectum can be determined and a fecal sample obtained in one operation by use of the instrument of this invention.

SUMMARY OF THE INVENTION

These and other objects of the invention are provided in a new and improved combined thermometer and fecal sampling apparatus which is characterized in a first preferred embodiment by an enlarged, generally cylindrical proximal end or handle removably enclosing a temperature measuring device such as a digital thermometer and having a temperature window for displaying body temperature. The handle is also provided with a water-resistant or waterproof cap threaded in the handle and a flexible plastic or rubber membrane covering a button switch which extends through the cap and activates the thermometer. Multiple longitudinal gripping splines or knurls and an elongated, hollow probe extend from the handle and the probe terminates in an ovoid loop, with a thermistor located in the Hall of the probe between the ovoid loop and the handle. Wiring is also provided for connecting the thermistor to the thermometer, wherein a fecal sample can be obtained from the rectum and the temperature of the animal can be measured in a single operation.

BRIEF DESCRIPTION OF THE DRAWING

The invention will be better understood by reference to the accompanying drawing, wherein.

DESCRIPTION OF THE PREFERRED EMBODIMENTS

Figure 1:
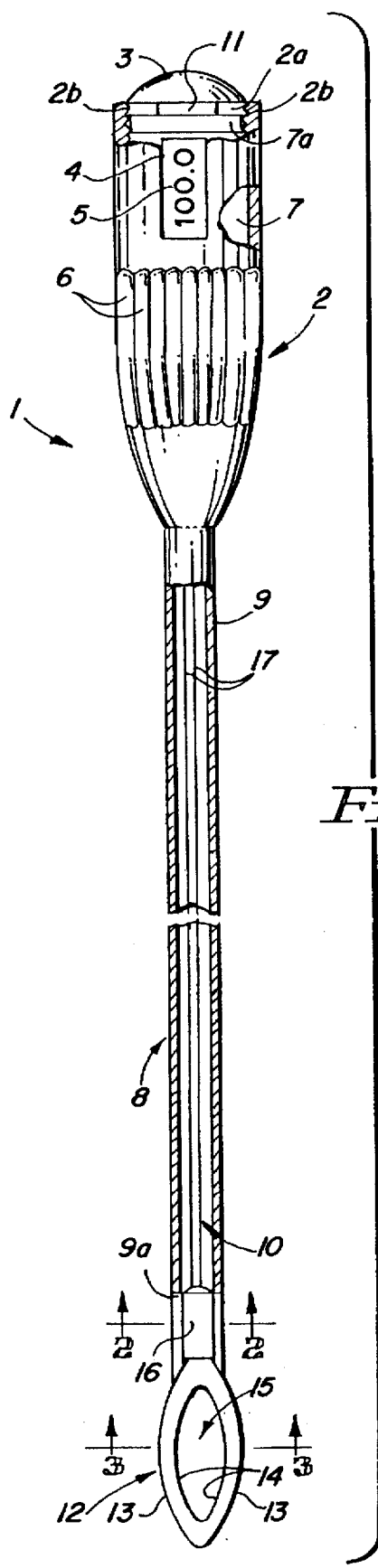
FIG. 1 is a front view, partially in section, of a preferred embodiment of the combined thermometer and fecal sampling device of this invention.

Referring initially to FIG. 1 of the drawing, in a preferred embodiment the combined thermometer and fecal sampling apparatus, hereinafter called the "apparatus", is represented by reference numeral 1. The apparatus 1 includes a cylindrical handle 2, fitted with a handle cap 2a, provided with cap threads 2b for engaging corresponding threads (not illustrated) in the handle 2. A flexible switch cover 3, which may be typically constructed of plastic, rubber or other flexible material, is attached to the handle cap 2a and overlays a start-stop button switch 11 extending through the handle cap 2a for energizing a thermometer such as a digital thermometer 7, enclosed within the handle 2 along with a battery 7a. A temperature display window 4 is provided in the handle 2 for displaying the temperature 5 when the apparatus 1 is in use, as hereinafter further described. In a preferred embodiment multiple, longitudinal grip serrations, knurls or splines 6 are provided in the handle 2 for gripping purposes and an elongated probe 8 extends from the handle 2 and terminates in a fecal sampler 12. In a most preferred embodiment the probe 8 is characterized by a thin probe wall 9 which defines a probe bore 10, through which wiring 17 extends from the digital thermometer 7 in the handle 2 and the opposite end of the wiring 17 terminates in a thermistor 16, positioned in a probe window 9a of the probe 8, between the fecal sampler 12 and the handle 2.

Figure 2:
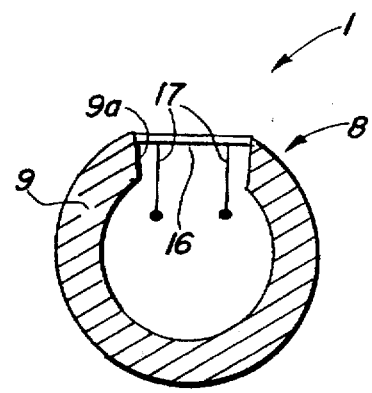
FIG. 2 is an enlarged sectional view taken along line 2—2 at the thermistor of the apparatus illustrated in FIG. 1.
Figure 3:
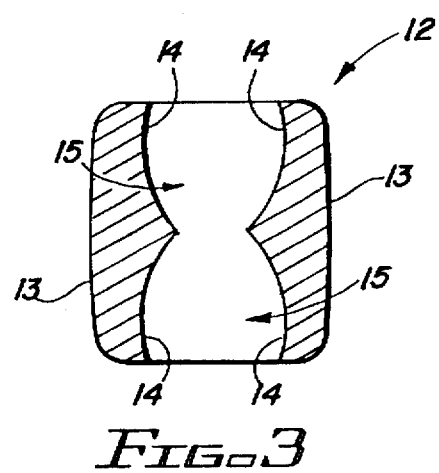
FIG. 3 is an enlarged sectional view taken along line 3—3 of the apparatus illustrated in FIG. 1, more particularly illustrating the fecal sampling ovoid loop element of the apparatus.

Referring now to FIGS. 1–3 of the drawings, in a most preferred embodiment of the invention the fecal sampler 12 is characterized by an ovoid loop 13, having an ovoidal cavity 15 defined by facing concave collection surfaces 14, as further illustrated in FIG. 3. Accordingly, it will be appreciated by those skilled in the art that when the probe 8 is inserted in the rectum of an animal, the thermistor 16 operates to sense the temperature of the animal and the digital thermometer 7 determines the temperature, while the fecal sampler 12 facilitates sampling of the fecal material in the rectum by rotation of the handle 2 and the ovoid loop 13 to capture a sample of the fecal material in the ovoidal cavity 15. Display of the rectal temperature is effected by pressing the switch cover 3, which in turn, activates the button switch 11 of the digital thermometer 7 enclosed inside the handle 2 and causes the temperature 5 to appear in the temperature display window 4 of the handle 2.

Referring again to FIGS. 1 and 3 of the drawings, it will be appreciated by those skilled in the art that the efficient capture of a significant quantity of fecal material for analyzing purposes is possible in the ovoidal cavity 15 by means of the concave collection surfaces 14 in the ovoidal loop 13. The concave collection surfaces 14 serve not only to scoop and accumulate solid fecal material and force it into the ovoidal cavity 15, but also to create surface tension when contacting liquid fecal material in order to maintain the liquid fecal material in the ovoidal cavity 15. Accordingly, it will be further appreciated that the concave shaping of the collection surfaces 14 further aids in obtaining significant fecal material for analysis under circumstances where the fecal material is loose and not well compacted and is therefore ordinarily difficult to collect. It will be further appreciated that the apparatus 1 serves not only to facilitate obtaining an accurate, dependable and fast temperature measurement from the rectum by means of the thermistor 16 and attached digital thermometer 7 in the handle 2, but also rapid and efficient collection of fecal material of any consistency in the ovoidal cavity 15 of the ovoidal loop 13 by rotation of the handle 2 in either direction by the user.

In another preferred embodiment of the invention the entire apparatus 1, including the handle 2, probe 8 and the ovoidal loop 13 of the fecal sampler 12 is constructed of a smooth, preferably satin-finish plastic material, typically molded in a one-piece injection molding process or otherwise, according to the knowledge of those skilled in the art. Furthermore, the digital thermometer 7 or a thermometer of alternative design, the button or pressure switch 11 extending through the threaded handle cap 2a of handle 2 and the cooperating thermistor 16 provided in the probe window 9a of the probe 8 above the fecal sampler 12, may be of any suitable design, also according to the knowledge of those skilled in the art. Activation of the digital thermometer 7 by means of pressure applied to the switch cover 3 facilitates one-hand operation of the button switch 11 in the apparatus 1 and instant display of the animal's temperature in the temperature display window 4. Furthermore, the apparatus 1 is quickly and easily cleaned and re-used by virtue of its unitary, water-resistant or waterproof construction and the concave, surface tension-inducing shape of the collection surfaces 14 in the ovoidal loop 13 of the fecal sampler 12 facilitates surprisingly efficient sampling of fecal material with a simple turn of the handle 2 in either direction by gripping the grip splines 6. Accordingly the apparatus 1 is highly practical, in that it is easy to use, causes minimum trauma to animals and decreases collection time, as well as cleanup time, therefore increasing doctor and technician efficiency. The device significantly decreases the physical and emotional trauma in the animal examined, since only a single penetration need be made to accomplish both temperature determination and fecal sampling.

While the preferred embodiments of the invention have been described above, it will be recognized and understood that various modifications may be made in the invention and the appended claims are intended to cover all such modifications which may fall within the spirit and scope of the invention.

Having described my invention with the particularity set forth above, what is claimed is:

1. A combined thermometer and fecal sampling apparatus for determining the temperature of animals and obtaining fecal samples in animals in a single rectal penetration, said apparatus comprising a handle; a thermometer provided in said handle for determining the temperature of the animals; a temperature display window provided in said handle for displaying the temperature of the animals; elongated probe means extending from said handle for insertion in the rectum of the animals; ovoid loop means provided on said elongated probe means and a pair of concave engaging surfaces shaped in said ovoid loop means for collecting the fecal samples from the rectum of the animals; and thermistor means provided in said probe means, said thermistor means electrically connected to said thermometer for sensing the temperature of the animals as the fecal sample is collected in said ovoid loop means.

2. The combined thermometer and fecal sampling apparatus of claim 1 wherein said thermistor means is positioned in said probe means adjacent to said ovoid loop means.

3. The combined thermometer and fecal sampling apparatus of claim 1 comprising grip means provided on said handle for securely gripping said handle.

4. The combined thermometer and fecal sampling apparatus of claim 3 wherein said thermistor means is positioned in said probe means adjacent to said ovoid loop means.

5. A combined thermometer and fecal sampling apparatus for determining the temperature of an animal and obtaining a fecal sample from the animal in a single rectal penetration, said apparatus comprising a handle; a cap threaded in said handle; a digital thermometer provided in said handle for determining the temperature of the animal; a temperature display window provided in said handle for displaying the temperature of the animal; an elongated, hollow probe extending from said handle for insertion in the rectum of the animal; an ovoid loop provided on said elongated probe and a pair of concave engaging surfaces shaped in said ovoid loop for collecting the fecal sample from the animal; and a thermistor provided in said probe, said thermistor electrically connected to said digital thermometer for sensing the temperature of the animal as the fecal sample is collected in said ovoid loop.

6. The combined thermometer and fecal sampling apparatus of claim 5 wherein said thermistor is positioned in said probe adjacent to said ovoid loop.

7. The combined thermometer and fecal sampling apparatus of claim 5 wherein
said thermistor is positioned in said probe adjacent to said ovoid loop.

8. The combined thermometer and fecal sampling apparatus of claim 5 comprising grip means provided on said handle for securely gripping said handle.

9. A combined thermometer and fecal sampling apparatus for determining the temperature of an animal and obtaining a fecal sample from the animal, said apparatus comprising a generally cylindrical handle; a cap provided in said handle and a switch cover provided on said cap; a digital thermometer having a battery and a pressure-sensitive switch provided in said handle for determining the temperature of the animal, said switch engaging said switch cover; a temperature display window provided in said handle for displaying the temperature of the animal responsive to pressure applied to said switch; an elongated hollow probe extending from said handle for insertion in the rectum of the animal; an ovoid loop provided on said elongated probe, said ovoid loop having a pair of concave engaging surfaces for collecting a fecal sample from the animal; a probe window provided in said probe; and a thermistor provided in said probe, said thermistor electrically connected to said digital thermometer for sensing the temperature of the animal as the fecal sample is collected.

10. The combined thermometer and fecal sampling apparatus of claim 9 wherein said thermistor is positioned in said probe window adjacent to said ovoid loop.

11. The combined thermometer and fecal sampling apparatus of claim 9 wherein
said thermistor is positioned in said probe window adjacent to said ovoid loop.

12. The combined thermometer and fecal sampling apparatus of claim 11 wherein said cap is threaded in said handle.

* * * * *